United States Patent
Allen

(10) Patent No.: US 6,643,110 B2
(45) Date of Patent: *Nov. 4, 2003

(54) STRESS-FOLLOWER CIRCUIT CONFIGURATION

(75) Inventor: Michael J. Allen, Rescue, CA (US)

(73) Assignee: Intel Corporation, Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/015,727

(22) Filed: Nov. 1, 2001

(65) Prior Publication Data

US 2002/0044400 A1 Apr. 18, 2002

Related U.S. Application Data

(63) Continuation of application No. 09/096,283, filed on Jun. 11, 1998, now Pat. No. 6,351,358.

(51) Int. Cl.[7] .................................................. H02H 3/20
(52) U.S. Cl. ........................... 361/90; 327/381; 326/87
(58) Field of Search ........................... 361/90, 92, 91.1, 361/91.5, 56, 111; 326/23, 24, 26, 27, 80, 87, 81, 83, 86, 30, 31; 327/108, 321, 380, 381, 384

(56) References Cited

U.S. PATENT DOCUMENTS

| | | | |
|---|---|---|---|
| 5,546,016 A | 8/1996 | Allen | 326/30 |
| 5,576,635 A | 11/1996 | Partovi et al. | 326/27 |
| 5,726,589 A * | 3/1998 | Cahill et al. | 326/81 |
| 5,731,714 A | 3/1998 | Monk et al. | 326/83 |
| 5,804,998 A | 9/1998 | Cahill | 326/83 |
| 5,852,540 A | 12/1998 | Haider | 326/86 |
| 5,874,836 A * | 2/1999 | Nowak et al. | 326/83 |
| 6,028,449 A * | 2/2000 | Schmitt | 326/80 |
| 6,054,875 A | 4/2000 | Wayner | 326/83 |
| 6,225,642 B1 * | 5/2001 | Liao | 257/3 |

* cited by examiner

Primary Examiner—Ronald W. Leja
(74) Attorney, Agent, or Firm—Kevin A. Reif

(57) ABSTRACT

Briefly, in accordance with one embodiment of the invention, an integrated circuit includes: a stress-follower circuit configuration. The stress-follower circuit of the configuration is coupled to a pad of the integrated circuit. The stress-follower circuit configuration is coupled so as to reduce the voltage stress on the gate of a transistor in a transistor stack so that in operation the transistor in the stack tolerates an operating voltage approximately 1.5 volts above its nominal voltage. The transistor stack is also coupled to the pad.

13 Claims, 2 Drawing Sheets

Vertical drain N-Channel metal-oxide semiconductor (VDNMOS) transistor

STRESS-FOLLOWER CIRCUIT CONFIGURATION

RELATED APPLICATION

This patent application is a continuation of U.S. patent application Ser. No. 09/096,283, filed Jun. 11, 1998, titled "A Stress-Follower Circuit Configuration," by Allen, assigned to the assignee of the present invention, now U.S. Pat. No. 6,351,358.

BACKGROUND

1. Field

The invention is related to transistors, and more particularly, to a stress-follower circuit configuration to protect such transistors.

2. Background Information

As is well-known, transistors may suffer from Electrical Over Stress (EOS), which in this context refers to the application of voltages above the specified safe range of an electrical device, and may result in device degradation. This may occur, for example, when the transistor is employed in the manner using a significantly higher operating voltage than the native process transistors are able to tolerate. Native process transistors are the basic building blocks of a semiconductor process. For example, a 0.25 micron semiconductor fabrication process may have native transistors with specified operating voltages of 1.8 to 2.5 volts. However, if a technique or approach were devised in which these transistors could tolerate these higher operating voltages, this would allow devices and/or systems operating at higher voltages to be created using this technology. In today's environment typically legacy devices, components, or systems, such as those employing or combining with Peripheral Component Interconnect (PCI), Accelerated Graphics Port (AGP), or Dynamic Random Access Memory (DRAM), for example, employ higher voltages than state-of-the art transistors fabricated using native processes.

SUMMARY

Briefly, in accordance with one embodiment of the invention, an integrated circuit includes: a stress-follower circuit configuration. The stress-follower circuit of the configuration is coupled to a pad of the integrated circuit. The stress-follower circuit configuration is coupled so as to reduce the voltage stress on the gate of a transistor in a transistor stack so that in operation the transistor in the stack tolerates an operating voltage approximately 1.5 volts above its nominal voltage. The transistor stack is also coupled to the pad.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

As previously described, and as is well-known, transistors may suffer from Electrical Over Stress (EOS), which in this context refers to the application of voltages above the specified safe range of an electrical device, and may result in device degradation. This may occur, for example, in a situation in which a transistor is employed at a significantly higher operating voltage than the native process transistors are able to tolerate. Typically, this can occur when the transistors are employed in an interface because this is a common situation in which a particular operating voltage may be employed. Likewise, as is also well-known, operating voltages for circuits, particularly integrated circuits, have been declining over the last few years. As a result, a situation has arisen in which transistors are being manufactured in a native process that tolerates a lower operating voltage than legacy interface operating voltage levels for some transistor applications. For example, this is the case in some situations for interfaces that comply with, for example, the Peripheral Component Interconnect (PCI) Specification, version 2.1, available from the PCI Special Interest Group, 2575 NE Kathryn St #17, Hillsboro, Oreg. 97124, December 1997, the Accelerated Graphics Port (APG) Interface Specification, version 1, dated Aug. 1, 1996, or version 2.0, dated May 4, 1998, available from, for example, the AGP Implementors Forum or Intel Corp, or that comply with Dynamic Random Access Memory (DRAM), which may employ in the range of 3 to 5 volts. In one particular situation, although the intention is not limited in scope to this particular situation, a legacy interface voltage level for input-output (I/O) operation is about 3.3 volts, whereas in some state-of-the art transistor fabrication processes the native voltage level is on the order of 1.8 volts, for example. Of course, it is not intended to limit the scope of the invention to state-of-the-art fabrication processes. It would be desirable if the transistors could be modified or employed in a manner that allowed them to operate at such legacy interface voltage levels with reliability and with reduced risk of damage due to a high or relatively higher operating voltage.

Figure 1:
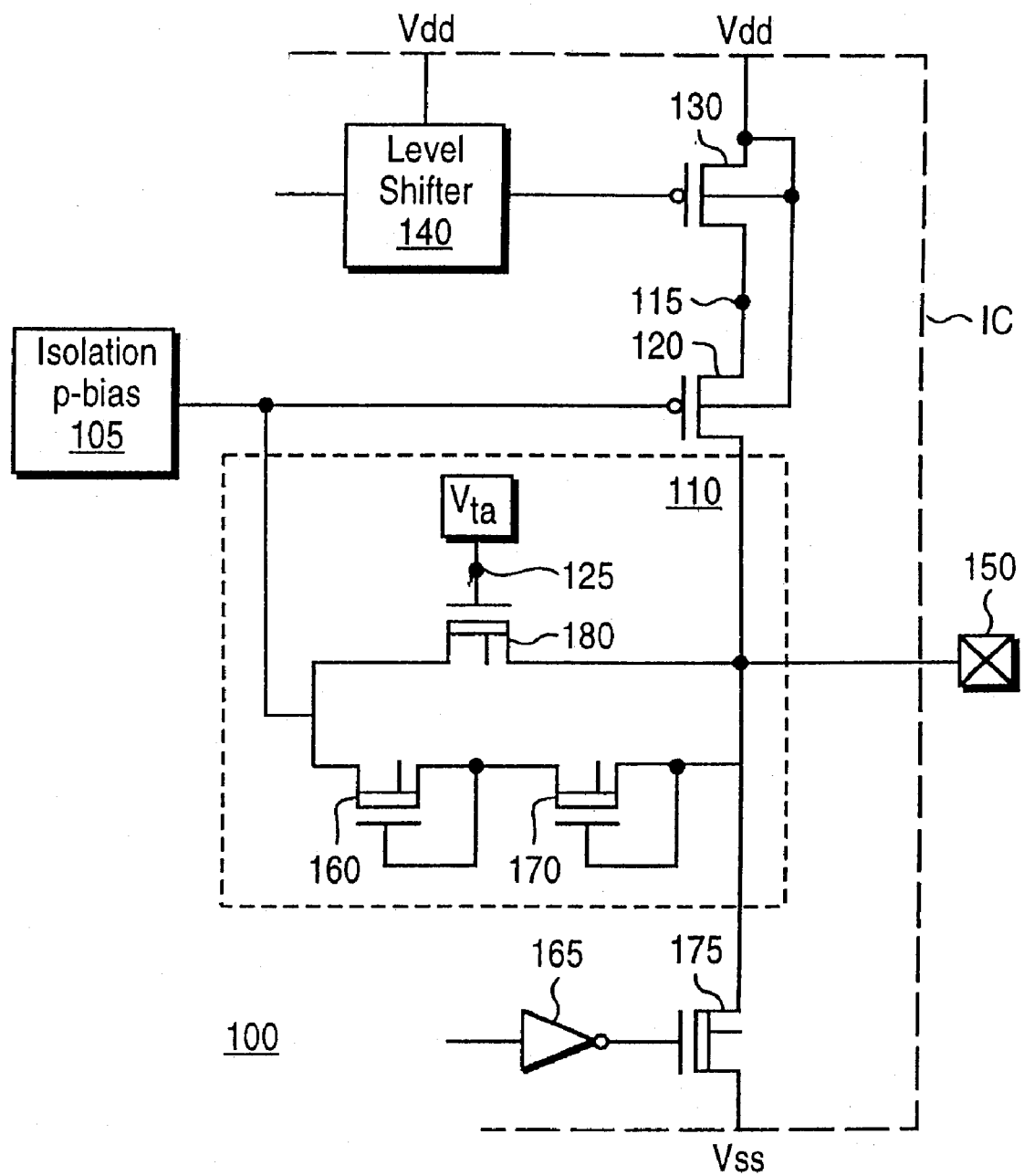
FIG. 1 is a circuit diagram illustrating an embodiment of a stress-follower circuit configuration in accordance with the present invention.
Figure 2:
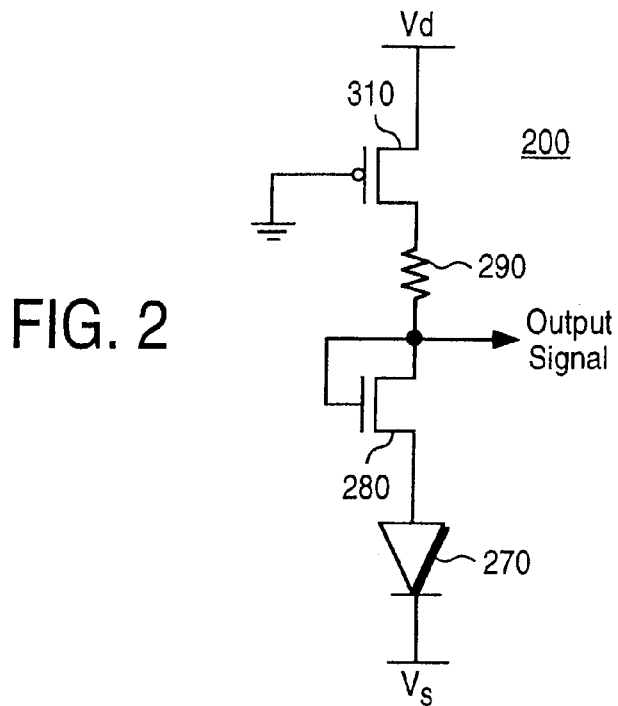
FIG. 2 is a circuit diagram of an embodiment of a bias voltage source that may be employed in the embodiment illustrated in FIG. 1.

FIG. 1 is a circuit diagram illustrating an embodiment 100 of a stress-follower circuit configuration in accordance with the present invention. This particular stress-follower circuit configuration embodiment includes the stress-follower circuit embodiment illustrated, and additional components. This embodiment is illustrated on an integrated circuit (IC) chip. The invention, of course, is not limited in scope to this particular embodiment. Therefore, alternative embodiments may include only an embodiment of a stress-follower circuit in accordance with the invention or more than just an embodiment of a stress-follower circuit, and these alternatives may also be embodied on an IC, embodied on more than one IC, or not embodied on an IC at all, for example. For the embodiment illustrated in FIG. 1, a two transistor stack is illustrated as coupled to a voltage $V_{dd}$. In this particular embodiment, these transistors comprise P-channel metal-oxide semiconductor (MOS) transistors, such as 120 and 130, as illustrated in FIG. 1. Therefore, the stack comprises a pull-up stack; however, the invention is not limited in scope in this respect. For example, alternatively, the stack may comprise N-channel transistors and may operate as a pull-down stack instead. For the embodiment illustrated in FIG. 1, bias voltage clamps are applied to the gates of the transistors of the stack. For example, an isolation bias 105 is applied to the gate of transistor 120 and a level shifter 140 is applied to the gate of transistor 130. A level shifter in this context comprises a circuit that changes a logical signal at one voltage level to an appropriate voltage level for use elsewhere. As only one example, it may change ground to a 1.8 voltage signals used in core logic to 1.5 to 3.3 voltage signal levels used in an output circuit. Level-shifters are well-known circuit blocks and need not be described in additional detail here. Any one of a variety of possibilities will provide satisfactory operation. Circuit configurations for producing a bias voltage source are also well-known in the art and will not be described in great detail here. Any one of a variety of bias voltage sources or bias generator circuits may be employed. FIG. 2, without limitation, illustrates one such embodiment. The output voltage in this embodiment is the sum of the voltage across the diode and the voltage across the N-channel metal-oxide semiconductor (NMOS) transistor. In addition, as another example, a bandgap circuit might be employed, although the voltage produced may or may not be useful, depending on the particular embodiment of the invention. As shall be explained in greater detail below, the bias voltage clamps are coupled in the circuit so that the bias voltage "automatically" accounts or adjusts for pad voltage excursions, that is, pad voltage overshoots or undershoots from the power rails of the circuit. In this particular embodiment in accordance with the invention, it is desirable to reduce the stress due to voltage on the isolation layers or gates of transistors 120 and 130 when these excursions occur. In this embodiment, the isolation layers comprise oxide gates, although the invention is not limited in scope in this respect.

Embodiment 100, as illustrated in FIG. 1, includes stress-follower circuit 110. As illustrated in this particular embodiment, when embodied on an IC, the stress-follower circuit is coupled to a pad of the IC, here 150. As previously suggested, the stress-follower circuit is coupled here so as to reduce the voltage stress across the gate of the transistors in a two transistor stack, so that in operation the transistors in the stack tolerate an operating voltage exceeding their nominal or native voltage. Likewise, the two transistor stack is also coupled to pad 150 in this particular embodiment. In this particular embodiment, the stress-follower circuit allows the transistors in the stack to tolerate an operating voltage approximately 1.5 volts above their nominal voltage. For example, although the invention is not limited in scope in this respect, transistors 120 and 130 have a nominal or native voltage of approximately 1.8 volts, whereas for this particular embodiment the operating voltage is approximately 3.3 volts.

Figure 3:
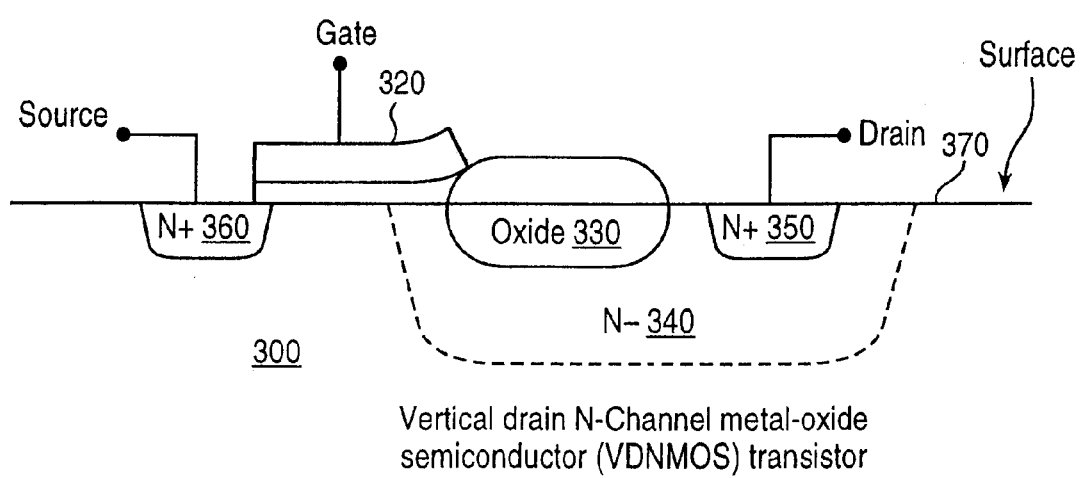
FIG. 3 is a schematic diagram illustrating an embodiment of a vertical drain metal-oxide transistor (VDMOS), such as may be employed in the embodiment of FIG. 1.

For the stress-follower circuit illustrated in FIG. 1, the transistors employed comprise vertical drain metal-oxide semiconductors field effect transistors (hereinafter, VDMOS transistors). Of course, the invention is not limited in scope in this respect. In one embodiment, VDMOS transistors may be formed by coupling the drain node of a transistor to the channel of the transistor through a lightly doped well layer which passes underneath a field oxide isolation layer and couples vertically up into the transistor channel. This reduces the high electric field at the drain/gate interface, and allows higher drain voltages without substantial of the transistor gate. This embodiment is illustrated in FIG. 3 and comprises a drain and channel formation that allows such transistors to withstand higher voltages than native transistors. For example, in a nominal 1.8 volt fabrication process, it would not be unusual for such transistors to tolerate greater than six volts.

For the embodiment illustrated in FIG. 1, isolation voltage bias 105 is applied to the gate of transistor 120 of the stack. As illustrated, transistor 120 is directly coupled to pad 150, whereas transistor 130 is coupled to the pad indirectly via transistor 120. Furthermore, three VDMOS transistors, 160, 170, and 180, couple pad 150 to isolation bias 105 in this particular embodiment. For example, transistor 180 couples between bias 105 and pad 150. A bias is applied to the gate of transistor 180. In this embodiment, the bias voltage applied comprises a semiconductor threshold voltage deviation from a source operating voltage for the integrated circuit, in this embodiment one threshold voltage for an N-channel transistor above $V_{ss}$. Of course, in an alternative embodiment, such as where a P-channel transistor is employed, for example, a different bias voltage may be applied. Likewise, two VDMOS transistors, 160 and 170 for this particular embodiment, as illustrated in FIG. 1, are coupled together with each coupled in a diode configuration. Likewise, these two transistors, 160 and 170, together couple between pad 150 and isolation bias 105 in this embodiment. It is noted that for the embodiment illustrated in FIG. 1, transistor 175 also comprises a VDMOS transistor, although, again, alternative embodiments are possible and, therefore, the invention is not restricted in scope in this respect.

As previously indicated, the circuit configuration of FIG. 1 is employed to reduce voltage stress on the isolation layers or gates as the pad voltage overshoots or undershoots the power rails for the circuit. For example, when the pad voltage is driven "low," the stress-follower circuit in this embodiment pulls the voltage of bias 105 lower. Likewise, when the pad voltage overshoots $V_{dd}$, the stress-follower circuit pulls the bias voltage higher. However, nominally the bias, 105, is set to the native voltage level.

Specifically, on voltage overshoots above $V_{dd}$, when the pad receives an input voltage signal, transistors 160 and 170, due at least in part to the diode configuration employed, pull the bias node voltage up, thereby reducing the stress across the gate oxide of transistor 120. Alternatively, if the pad voltage undershoots, the bias node voltage is pulled lower via transistor 180, to again reduce the stress on the gate oxide of transistor 120. For transistor 130, alternatively, its gate in this embodiment is tied, via level shifter 140, to a semiconductor threshold voltage down from a drain operating voltage, which in this particular embodiment is $V_{dd}$ minus a P-channel transistor threshold voltage. When the voltage of pad 150 undershoots, the intermediate node, designated 115 in FIG. 1, is also pulled somewhat lower. Thus, the drain/gate interface of transistor 120 experiences little or no overstressed. If node 115 is designed such that it does not drop more than the native process voltage, which in this example is 1.8 volts, although the invention is not limited in scope in this respect, plus one p-channel threshold voltage, down from $V_{dd}$, then the gate/source interface of device 130 also experiences little or no overstress. Thus, the voltage stresses at device 130 are maintained in the range of the native process, which in this case is 1.8 volts, although, again, the invention is not limited in scope in this respect.

This operation also allows the transistor stack to be employed as an MOS clamp for the pad. In this regard, see, for example, U.S. Pat. No. 5,546,016, titled "MOS Termination for Low Power Signaling," by M. Allen, issued Jul. 3, 1995, assigned to the assignee of the present invention.

One advantage of this embodiment is that it allows a significantly higher operating voltage relative to native process voltage capability with acceptable EOS and reliability risk. Whereas typical approaches allow about 1.4 times operating voltage over native voltage, this approach allows two times operating voltage over native voltage. Other advantages of this approach is neither extra pins nor power supplies are employed to achieve its results. Therefore, by employing this particular embodiment, leading edge circuit products may be manufactured using lower voltage native processes and continue to interface with devices, components or systems employing higher, legacy operating voltages, such as, for example, 3.3 volt buses and other such systems.

An embodiment of a method of reducing the voltage stress on the isolation layer of a transistor coupled to the pad of an integrated circuit in accordance with the present invention is as follows. A voltage bias is applied to or coupled to the isolation layer of the transistor, such as illustrated in FIG. 1, for example. Likewise, another port of the transistor, such as the drain or source, is coupled to the pad. The voltage bias is also coupled to the pad via one or more semiconductor devices capable of tolerating a voltage greater than the nominal transistor operation voltage, such as, for example, as illustrated in FIG. 1, VDMOS transistors. Therefore, as previously explained, the pad bias "automatically" adjusts to reduce the stress on the isolation layer of the transistor. Of course, the invention is not limited in scope to this particular embodiment.

While certain features of the invention have been illustrated as described herein, many modifications, substitutions, changes and equivalents will now occur to those skilled in the art. It is, therefore, to be understood that the appended claims are intended to cover all such modifications and changes as fall within the true spirit of the invention.

What is claimed is:

1. An integrated circuit comprising:
    a stress-follower circuit configuration;
    the stress-follower circuit configuration being directly connected to a pad of the integrated circuit;
    the stress-follower circuit configuration being coupled so that in operation a transistor in a transistor stack tolerates approximately 1.5 volts above its nominal voltage;
    the transistor stack also being coupled to the pad.

2. The integrated circuit of claim 1, wherein an isolation layer comprises a gate and the transistors in the transistor stack comprise metal-oxide semiconductor transistors.

3. The integrated circuit of claim 2, wherein the nominal voltage comprises approximately 1.8 volts and an operating voltage comprises approximately 3.3 volts.

4. The integrated circuit of claim 2, wherein the transistor(s) of the stress follower circuit configuration comprise vertical drain metal-oxide semiconductor field effect transistors(s) (VDMOS transistor(s)).

5. The integrated circuit of claim 2, wherein the transistor stack comprises one of a p-channel transistor stack and an n-channel transistor stack.

6. The integrated circuit of claim 2, wherein the transistor stack comprises a two transistor stack;
    the stress-follower circuit configuration being coupled to reduce the voltage stress on the gate of both transistors in the stack.

7. An integrated circuit as recited in claim 1, further comprising:
    a bias voltage clamp circuit connected to a transistor in said transistor stack; wherein said stress follower circuit comprises:
        a first transistor connected between said bias voltage clamp circuit and said pad; and
        a pair of transistors connected in a diode configuration between said bias voltage clamp and said pad.

8. An integrated circuit as recited in claim 7, further comprising:
    a second bias voltage circuit connected to a gate of said first transistor.

9. A method of reducing voltage stress on the isolation layer of a transistor coupled to the pad of an integrated circuit including the transistor comprising:
    coupling the isolation layer of the transistor to a voltage bias clamp and coupling another port of the transistor to the pad; and
    coupling the voltage bias clamp to the pad via one or more transistors, each of said one or more transistors being structured to tolerate a voltage greater than the nominal transistor operating voltage.

10. The method of claim 9, wherein the transistor comprises a metal-oxide semiconductor transistor, the isolation layer comprises a gate and the other port comprises one of a drain and a source.

11. The method of claim 10, wherein the one or more transistors capable of tolerating a voltage greater than the nominal transistor operating voltage comprise one or more vertical drain metal-oxide semiconductor transistors.

12. A method of reducing voltage stress on the isolation layer of a transistor coupled to the pad of an integrated circuit including the transistor as recited in claim 10, wherein said coupling the voltage bias clamp to the pad via one or more transistors comprises:
    coupling a first transistor between said voltage bias clamp and the pad; and
    coupling a second transistor and a third transistor in a diode configuration between said voltage bias clamp and said pad.

13. A method of reducing voltage stress on the isolation layer of a transistor coupled to the pad of an integrated circuit including the transistor as recited in claim 12, further comprising:
    coupling a voltage bias to a gate of said first transistor.

* * * * *